United States Patent [19]

Assmus et al.

[11] Patent Number: 5,169,967
[45] Date of Patent: Dec. 8, 1992

[54] ALUMINUM MAGNESIUM HYDROXY FATTY ACID COMPOUNDS AND THERMOSTABLE LIPOGELS INCLUDING SAME

[75] Inventors: Uwe Assmus, Reinheim; Klaus Schanz, Dannstandt-Schauernheim; Bruno Kaumann, Frankenthal, all of Fed. Rep. of Germany

[73] Assignee: Giulini Chemie GmbH, Ludwigshafen/Rh, Fed. Rep. of Germany

[21] Appl. No.: 588,575

[22] Filed: Sep. 26, 1990

[30] Foreign Application Priority Data

Sep. 28, 1989 [DE] Fed. Rep. of Germany ....... 3932377

[51] Int. Cl.$^5$ .............................................. C11C 1/00
[52] U.S. Cl. ........................................ 554/71; 554/76; 424/68; 424/686
[58] Field of Search .................. 260/414; 424/68, 686; 554/71, 76

[56] References Cited

U.S. PATENT DOCUMENTS 4,434,076 2/1984 Mardis et al. ..................... 252/315.2
4,724,098 2/1988 Kalz et al. ......................... 252/315.2

FOREIGN PATENT DOCUMENTS 0204240 12/1986 European Pat. Off. .
3145449 7/1982 Fed. Rep. of Germany .

OTHER PUBLICATIONS

Jordan, J. W., "Organophilic Bentonites.I", *Jour. Phys. and Colloid Chem.*, vol. 53, No. 294, (1949), pp. 294–306.

Chemical Abstracts, vol. 112, #18, p. 407, 1990 164736c.
Martin et al., Chemical Abstracts, vol. 112, #18, p. 407, 1990, 164736b.

*Primary Examiner*—Jose G. Dees
*Assistant Examiner*—D. D. Carr
*Attorney, Agent, or Firm*—Spencer, Frank & Schneider

[57] ABSTRACT

A novel aluminum magnesium hydroxy fatty acid compound is disclosed having a general formula, $Al_x Mg_y(OH)_{3x+2y-z}R_z \cdot nH_2O$, wherein R is at least one aliphatic monocarboxylic acid group having the formula $RCOO^-$ and comprising from 12 to 22 carbon atoms, and wherein $x=2$, $2 \leq y \leq 10$, $z=2$, and n is an integer greater than zero. The compound is prepared by a process including placing water and a salt which is one of an alkali metal salt or an ammonium salt of at least one aliphatic monocarboxylic acid having from 12 to 22 carbon atoms in a reactor fitted with heating and stirring means. The salt is dissolved by intensive stirring and by heating to a temperature ranging from 20° to 90° C. to provide a salt solution. The pH of the salt solution in the reactor is maintained at a pH of at least 8 to provide an alkaline solution. A solution comprised of water, an aluminum salt, and a magnesium salt is added to the reactor under constant stirring to cause reaction and precipitation of a precipitate comprised of the novel aluminum magnesium hydroxy fatty acid compound. The precipitate is separated and washed with substantially demineralized water until substantially no anions of the aluminum salt and the magnesium salt are detectable. A lipogel with improved thermal stability is formed using the novel compound and organic lipophilic compounds which are liquid at room temperature, and is useful in cosmetic or pharmaceutical preparations.

17 Claims, 1 Drawing Sheet

ALUMINUM MAGNESIUM HYDROXY FATTY ACID COMPOUNDS AND THERMOSTABLE LIPOGELS INCLUDING SAME

BACKGROUND OF THE INVENTION

1. Field of the Invention.

The present invention relates to thermostable lipogels comprised of a novel aluminum magnesium hydroxy fatty acid compound and organic lipophilic compounds; and to the production of the novel aluminum magnesium hydroxy fatty acid compounds and the thermostable lipogels, as well as to the use of these thermostable lipogels in cosmetic and pharmaceutical preparations.

2. Background of the Related Art.

Gel compositions based on mineral clays which swell, such as montmorrilonites and bentonites, as well as so-called organically-modified bentonites are known; see, for example, Jordan, J. W., Jour. Phys. and Colloid Chem., 53, 294 (1949), or European Patent No. 204,240, which corresponds to U.S. Pat. No. 4,724,098, or Federal Republic of Germany Published Patent Application No. 3,145,449, which corresponds to U.S. Pat. No. 4,434,076, the disclosures of which are herein incorporated by reference.

Bentonites are colloidal, aluminum silicate clays composed chiefly of montmorillonite whose composition in turn is approximately $Al_2O_3.4SiO_2.nH_2O$. The organically-modified mineral clays are known to demonstrate a good swelling effect in oils, fats, and waxes, and form viscous gels in combination with them when formulated with the use of mechanical energy, suitable additives and suitable temperatures.

One great disadvantage of these prior art gel preparations, however, is that they contain very large amounts of substances which can have an irritating effect on skin and which are toxicologically not safe, including polar additives, such as organic polar additives including methanol and acetone, and quaternary ammonium salts introduced by ion exchange. In addition, prior art gel preparations have an inherent brown to beige color which is aesthetically displeasing and, for that reason, disadvantageous if the gel is used in cosmetic formulations.

Federal Republic of Germany Published Patent Application No. 3,732,265 to R. Martin, and co-inventors herein K. Schanz and B. Kaufmann teaches novel aluminum magnesium hydroxy compounds, particularly novel aluminum magnesium hydroxy carboxylates, which have a good swelling effect in oils, fats and waxes. These compounds have the general formula $Al_xMg_y(OH)_{3x+2y-z}R_z.nH_2$, in which $x=3$ to 9, $y=4$ to 13, $z=3$ to 5, and $3x+2y=35$, and in which R is an aliphatic monocarboxylic acid group having the formula $R_1COO^-$, and $R_1COO^-$ contains from 2 to 22 carbon atoms or represents a technical mixture of aliphatic monocarboxylic acid groups containing from 16 to 18 carbon atoms. The compounds function as gellants or gelling agents for certain liquids, in particular, for organic lipophilic compounds which are liquids at 20° C., with which they form gels. The amount of polar additive can be reduced when these compounds are employed to form gels and such gels are useful in cosmetic formulations.

These compounds are distinguishable from the prior art's organically-modified bentonites, however, not only by chemical composition, but also by structure. The structure of these aluminum magnesium hydroxy compounds is a so-called layered structure and is derived from brucite, $Mg(OH)_2$, in which the $OH^-$ ions are characterized by the closest packed hexagonal lattice and octahedral gaps therein are occupied by $Mg^{+2}$ cations. The layered structure results from having only every second strata of octahedral gaps occupied by metal atoms.

The replacement of bivalent Mg cations by trivalent aluminum in these aluminum magnesium hydroxy compounds leads to a surplus positive charge in the octahedral gaps which is balanced by aliphatic carboxylates anions in the intermediate layer. In contrast, organically-modified bentonites, which, being layered silicates, have an intermediate layer containing positively charged quaternary ammonium groups to counteract the charge.

These aluminum magnesium hydroxy compounds according to our previous invention, Federal Republic of Germany Published Patent Application No. 3,732,265, form gels in combination with a plurality of organic lipophilic compounds. Moreover, these gels have an absolutely pure white color unlike gels formed with organically-modified bentonites. Such gels are, of course, suitable for cosmetic formulations in which a pure white color is especially important and they contain no quaternary ammonium salts or groups and have a reduced quantity of polar additives. They are, for this reason, less irritating to the skin than corresponding formulations having an organically-modified bentonite base.

The production of gels from these aluminum magnesium hydroxy compounds is, however, not unproblematic, because it requires the use of complicated and expensive mixing assemblies that produce high shear forces, as mentioned in Federal Republic of Germany Published Patent Application No. 3,732,265. Further, the gels produced frequently are not stable enough against temperature effects. In heat stress tests, for example, these gels demonstrate a slight but distinct oil separation at approximately 50° C. The viscosity of the gels changes accordingly and is notably lower, as is the viscosity of cosmetic formulations prepared from the gels. A distinct oil separation is not usually acceptable in cosmetic formulations, however. Moreover, employment of such gels is not economical because the gels should also stablize the finished formulation and, if necessary, additionally, bind any oil therein.

Thus, the inventors continued to seek an improved gel preparation which meets the requirements of (1) substantially no temperature-induced separation of oil, (2) sufficiently high viscosity at elevated storage temperatures on the order of, for example, 50° C., and storability for at least three months, (3) easy reproducibility and economic production, and (4) no content of polar additives or quaternary ammonium salts or groups.

SUMMARY OF THE INVENTION

The problem posed was solved in a surprising manner by means of a gel preparation which contains an organic lipophilic compound which is liquid at room temperature (20° C.), and, as a gel-forming agent, a new aluminum magnesium hydroxy fatty acid compound.

The new aluminum magnesium hydroxy fatty acid compound for the gel preparation, has a so-called layered structure as previously discussed and is represented by the general formula:

$$Al_xMg_y(OH)_{3x+2y-z}R_z \cdot nH_2O$$

wherein R denotes at least one aliphatic monocarboxylic acid group having the formula RCOO— and comprising from 12 to 22 carbon atoms, and wherein $x=2$, $2 \leq y \leq 10$, $z=2$ and n is an integer greater than zero. Thus, the group R may have a formula represented by RCOO— or, when the compound contains a mixture of such groups, by RCOO—, R'COO— etc., in which R, R', etc. are different aliphatic monocarboxylic acid groups.

The new compounds may be obtained by reacting a soluble aluminum salt with a soluble magnesium salt in an alkaline aqueous medium at a pH value of $\geq 8$ in the presence of an alkali or ammonium salt of an aliphatic monocarboxylic acid containing from 12 to 22 carbon atoms and its mixtures. Aqueous solutions of the aluminum and magnesium salts, respectively, are added simultaneously or are combined into one solution and added with intensive stirring to the alkaline, aqueous solution of the alkali or ammonium salt of an aliphatic monocarboxylic acid at temperatures ranging from 20° to 90° C.; preferably at temperatures ranging from 60° to 85° C. The term "intensive stirring" means constant, rapid stirring, but not stirring to produce high shear forces as was required in the inventors' prior Application. The pH of the solution must always be $\geq 8$. The precipitate obtained in this manner is separated according to any of several well known prior art methods, such as by filtration, and is washed with completely demineralized water until substantially no anions are detectable in the wash water from either the aluminum or magnesium salts used when tested by, for example, wet chemical techniques and, most preferably, no anions remain when tested by any technique. It is of particular importance to perform the reaction in the absence of carbon dioxide, water hardening compounds, and other foreign ions, e.g., by using completely degassed and demineralized water.

Thus, the novel aluminum magnesium hydroxy fatty acid compound according to the invention is prepared by a process including the steps of (a) placing water and a salt which is one of an alkali metal salt or an ammonium salt of at least one aliphatic monocarboxylic acid having from 12 to 22 carbon atoms in a reactor fitted with means for heating and means for stirring; (b) dissolving the salt by intensive stirring and by heating to a temperature ranging from 20° to 90° C. to provide a salt solution; (c) maintaining the pH of the salt solution at a pH of at least 8 to provide an alkaline solution having a pH of at least 8 and a temperature ranging from 20° to 90° C. in the reactor; (d) preparing an aqueous solution comprised of water and aluminum salt which is soluble in water and an aqueous solution comprised of water and a magnesium salt which is highly soluble in water; (e) adding the solutions of step (d) to the reactor containing the alkaline solution of step (c) simultaneously and with constant stirring to cause reaction of the aluminum salt, the magnesium salt and the salt which is one of an alkali metal salt or an ammonium salt of at least one aliphatic monocarboxylic acid, and to cause precipitation of a precipitate comprised of an aluminum magnesium hydroxy fatty acid compound; (f) separating the precipitate from the solution of step (e); and (g) washing the precipitate with water which has been substantially demineralized until substantially no anions of the aluminum salt and the magnesium salt are detectable.

Preferably the water employed throughout the process is substantially demineralized water so as to substantially exclude foreign ions from at least the reaction of step (e).

Halides, nitrates and sulfates of aluminum, as well as basic aluminum halides, for example, $Al_5(OH)_5Cl$, (ACH), and alkali metal aluminates, are suitable as water soluble aluminum compounds for these reactions. Corresponding magnesium compounds which may be used for these reactions include halides, nitrates, and sulfates of magnesium. Adjustment of the pH value of the solution during the reaction to maintain a pH of at least 8 should always be affected by addition of a solution of one of an alkali metal hydroxide or ammonium hydroxide. For reasons mentioned above, the absence of carbon dioxide should be ensured preferably at each step of the process. Carbon dioxide should especially be excluded from the reactor during the reaction of step (e). It is therefore recommended that the reaction of step (e) be carried out in a closed reactor, preferably with the use of an atmosphere of inert gas, such as nitrogen, and preferably the atmosphere of inert gas is employed also during steps (a) thru (d).

The novel aluminum magnesium hydroxy fatty acid compounds are finely crystalline, white, powdery substances. Their characterization, in particular detection of their layered structure, may be obtained with the help of an X-ray diffraction spectrum, (see the X-ray diffraction spectrum of FIG. 1 and Table 5 herein).

The organic monocarboxylic acids comprising from 12 to 22 carbons acids include compounds denoted by the general total formula $C_nH_{2n+2}COOH$, such as, for example, myristic acid, palmitic acid, and stearic acid, and also their mixtures, e.g., a mixture of palmitic and stearic acid, i.e., a C16/C18 mixture. These acids are commercially available or may be mixed as required without prior purification procedures.

The new aluminum magnesium hydroxy fatty acid compounds may be isolated by means of vacuum drying or spray drying. The filter cake, subsequent to washing, as well as the filter cake resuspended in water and spray-dried, may be used as starting material for the production of a gel.

The production of a gel is performed in a closed reactor having a stirring device; expensive stirrers which produce high shear forces not being required. The gellation reaction occurs quantitatively at temperatures between 90° and 130° C., under intensive stirring of the two components, and aided by the increased pressure which results from the increased partial pressure of water vapor, i.e., steam pressure.

Thus, a thermostable lipogel is produced which includes a novel aluminum magnesium hydroxy fatty acid compound according to the invention (constituent a); and at least one organic lipophilic compound which is liquid at room temperature (20° C.)(constituent b), prepared by a process including reacting constituents a and b at a temperature ranging from 90° to 130° C. and a pressure of at least 1 bar while intensively stirring same.

At least one compound from the following groups of materials may be used as the organic liphophilic compound for gelation with the new aluminum magnesium hydroxy fatty acid compound: a. vegetable and animal fats and oils, for example, lanolin, jojoba oil, and castor oil; b. paraffin hydrocarbons, for example, mineral oil and isoparaffins; c. silicone oils, for example, tetrameric- or pentameric-cyclomethicone; d. aliphatic and aromatic esters, for example, isopropyl myristate and isopropyl palmitate; and e. higher alcohols and ethers, for example, 2-Octyl dodecanol.

The thermostable lipogel has a concentration of the aluminum magnesium hydroxy fatty acid compound which ranges from 10 to 30 weight percent, and which is preferably 20 weight percent, with respect to the lipogel. The thermostable lipogel has a concentration of the organic lipophilic compound which ranges from 70 to 90 weight percent, and which is preferably 80 weight percent.

A lipogel produced in this manner is a colorless, highly viscous gel, which remains particularly stable with respect to its viscosity under the effect of heat. In particular, cosmetic preparations and pharmaceutical preparations produced with it do not show any oil separation.

BRIEF DESCRIPTION OF THE PREFERRED EMBODIMENTS

Figure 1:
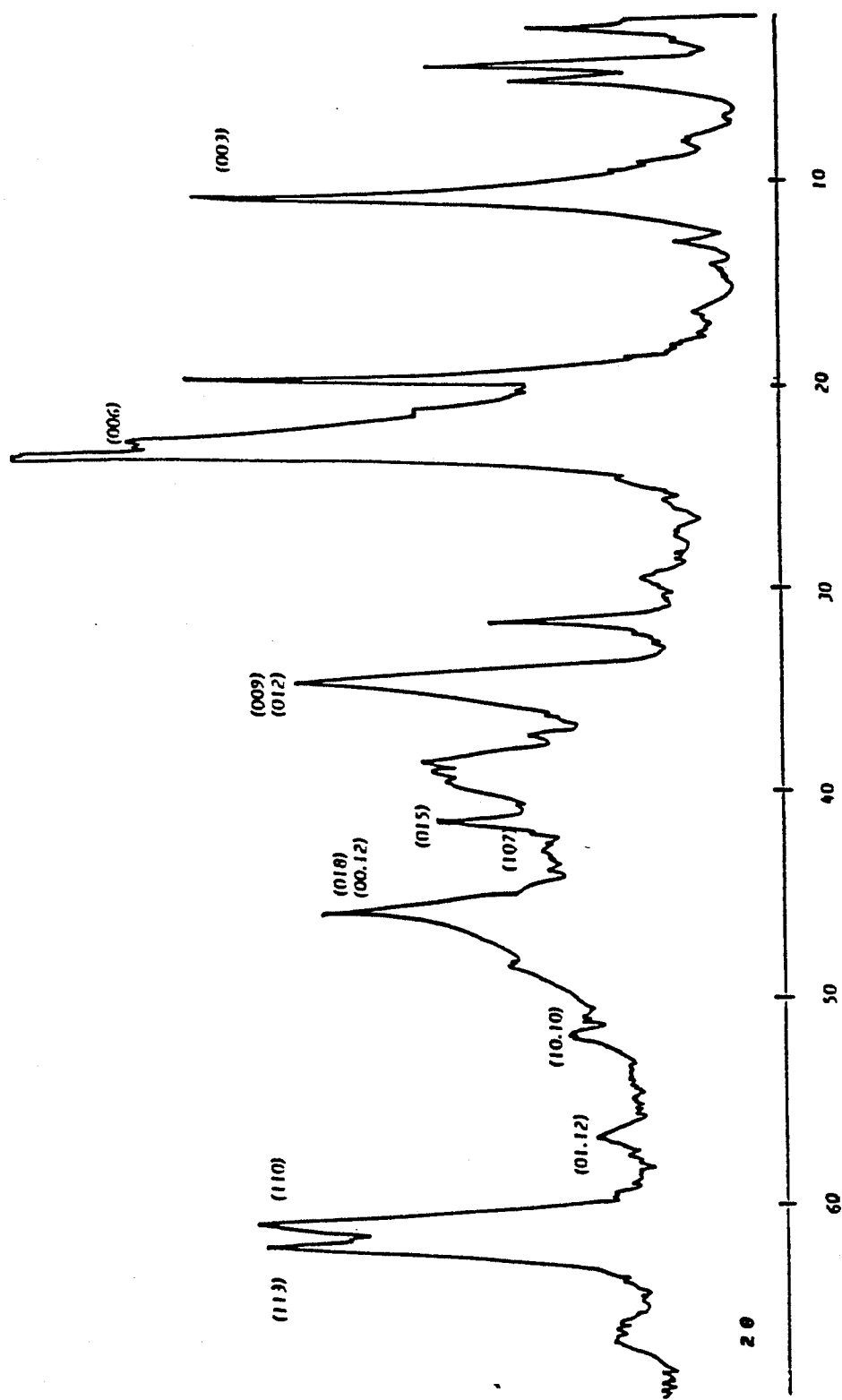
FIG. 1 is an X-ray diffraction spectrum of an aluminum magnesium hydroxy fatty acid compound according to the present invention, which is an aluminum magnesium hydroxy stearate according to Example 2.

The following Examples 1 thru 4 illustrate the production of new aluminum magnesium hydroxy fatty acid compounds.

EXAMPLE 1

Production of aluminum magnesium hydroxy stearate/palmitate, $$Al_2Mg_6(OH)_{16}(C_{17}H_{35}COO)_{1.3}(C_{15}H_{31}COO)_{0.7}.$$

8.73 kg of a commercial sodium stearate (65% C18/35% C16) was suspended in 182.1 l of completely demineralized water in a closed reactor containing an inert gas. The suspension was subsequently heated to 80° C. under stirring until the solution was clear. 29.55 kg of completely demineralized water was placed in a separate stirring container and 7.11 kg AlCl$_3$. 6H$_2$O and 17.94 kg MgCl$_2$.6H$_2$O were dissolved in it consecutively. The clear solution of AlCl$_3$/MgCl$_2$ and 54.6 kg of a 17.3% NaOH solution were simultaneously measured into the receiving vessel (a closed reactor) so that the pH value was always maintained above 8. After approximately one hour of stirring, a pH value of 9.8 was obtained. The suspension was cooled to room temperature and the insoluble aluminum magnesium hydroxide stearate/palmitate was filtered off.

Washing with completely demineralized water was continued until no more chloride ions could be detected by means of an AgNO$_3$ solution in this well-known wet chemical technique. Subsequently, the filter cake was dried, using a conventional device, such as a spray dryer, vacuum dryer, etc.

The yield obtained was 13.8 kg (92%); description, a white, finely crystalline powder having a chemical analysis: 5.31% Al dry substance (theoretically 5.29%), 14.34% Mg dry substance (theoretically 14.31%), and 54.02% C$_{17}$H$_{35}$COO/C$_{15}$H$_{31}$COOH dry substance (theoretically 53.7%).

EXAMPLE 2

$$Al_2Mg_6(OH)_{16}(C_{17}H_{35}COO)_2.$$

108.71 kg of completely demineralized water was placed in a closed reactor containing inert gas and 4.11 kg stearic acid (98% C$_{18}$) are suspended therein under stirring. Subsequently, 10.40 kg of 50% NaOH was added and heated to 80° C. under constant stirring. 14.48 kg of completely demineralized water were placed in a separate container and 3.49 kg of AlCl$_3$.6-H$_2$O and 8.81 kg of MgCl$_2$.6H$_2$O were dissolved consecutively. The clear solution was transferred into the receiving vessel over a period of 30 minutes under intensive stirring. After another 30 minutes of stirring, a pH value of 9.5 was obtained. The suspension was cooled to room temperature and the insoluble aluminum magnesium hydroxy stearate was filtered off.

Washing was performed using completely demineralized water until chloride ions could no longer be detected as AgCl by means of an AgNO$_3$ solution. The filter cake was subsequently dried by means of the usual devices, such as a spray dryer, vacuum dryer, etc.).

The yield obtained was 7.1 kg (94%); description, a white, finely crystalline powder having a chemical analysis: 5.23% Al dry substance (theorectically 5.19%), 14.13% Mg dry substance (theoretically 14.04%), 54.80% C17H35COOH dry substance (theoretically 54.57%).

EXAMPLE 3

Production of aluminum magnesium hydroxy behenate, $$Al_2Mg_4(OH)_{12}(C_{21}H_{43}COO)_2.$$

64.92 kg of completely demineralized water were placed in a closed reactor containing inert gas and 3.28 kg of behenate acid (98% C$_{22}$) were suspended therein under stirring. Subsequently, 7.66 kg of 50% KOH were added and heated to 80° C. under constant stirring. 17.88 kg of completely demineralized water were placed in a separate container and 2.33 kg AlCl$_3$.6H$_2$O and 3.93 kg MgCl$_2$.6H$_2$O were dissolved consecutively. The clear solution was transferred into the receiving vessel over a period of 30 minutes under intensive stirring. After another 30 minutes of stirring, a pH value of 10 was obtained. The suspension was cooled to room temperature and the insoluble aluminum magnesium hydroxy behenate was filtered off.

Washing was performed using completely demineralized water until chloride ion could no longer be detected as AgCl by means of an AgNO$_3$ solution. The filter cake was subsequently dried by means of the usual devices, such as a spray dryer, vacuum dryer, etc.

The yield obtained was 4.8 kg (96%); description, a white, finely crystalline powder having a chemical analysis: 5.18% Al dry substance (theoretically 5.22%), 9.35% Mg dry substance (theoretically, 9.40%), and 65.52% C$_{21}$H$_{43}$COOH dry substance (theoretically, 65.66%).

EXAMPLE 4

Production of magnesium hydroxy myristate, $$Al_2Mg_4(OH)_{12}(C_{13}H_{27}COO)_2.$$

60 kg completely demineralized water was placed in a closed reactor containing inert gas, and 2.81 kg of myristic acid (98% C$_{14}$) were suspended in it under continuous stirring. 9.67 kg 50% KOH were subsequently added and heated up to 80° C. under continuous stirring. 17.33 kg of completely demineralized water were placed in a separate container and 4.11 kg of $Al_2(SO_4)_3.18\ H_2O$ and 6 kg of $MgSO_4.7\ H_2O$ were dissolved consecutively over a period of 30 minutes. The clear solution was transferred under intensive stirring into the receiving vessel. After another 30 minutes of stirring, a pH value of 10 was obtained. The suspension was cooled to room temperature and the insoluble aluminum magnesium hydroxy myristate was filtered off. Washing with completely demineralized water was continued until no more sulfates in the form of $BaSO_4$ could be detected by means of a $BaCl_2$ solution in this well-known wet chemical technique. Subsequently, the filter cake was dried using a conventional device, such as a spray dryer, vacuum dryer, etc.).

The yield obtained was 4.7 kg (94%); description, a white, finely crystalline powder having a chemical analysis: 6.61% Al dry substance (theoretically 6.66%), 11.94% Mg dry substance (theorectically 12.00%), and 56.08 $C_{13}H_{27}COOH$ dry substance (theoretically, 56.14%).

The following Examples 5 to 8 describe the production of lipogels using the new aluminum magnesium hydroxy fatty acid compounds.

EXAMPLE 5

Production of a cyclomethicone lipogel.

236 kg of cyclomethicone pentamer (incl. 5% evaporation loss) and 83 kg of the vacuum dried, aluminum magnesium hydroxy stearate powder from Example 2 and having a moisture content of 10% were weighed into a closed 1 m³ mixer (Type: Becomix, Bremen) and homogeneously suspended over a period of 30 minutes with vigorous stirring. Subsequently, the suspension was heated to 110° C., which resulted in the formation of a vapor pressure, i.e., a steam pressure, of approximately 2.0 bar. These conditions were maintained for 30 minutes. Subsequently, a vacuum was drawn and regulated so that the temperature did not drop significantly below 105° C. The gel formation process was complete when the water was completely evaporated; i.e., under vacuum a constant temperature of 110° was established. The water/cyclomethicone mixture evaporated during gel production was condensed and separated so that the cyclometyhicone could be reused in a further reaction.

Subsequently, the gel was cooled to 80° C. and the product was filled into barrels. In these containers, the finished gel was cooled to room temperature.

The yield of white, cyclomethicone lipogel obtained was 261 kg (87%).

EXAMPLE 6

Production of an isopropyl palmitate lipogel.

225 kg of isopropyl palmitate and 88 kg of the vacuum dried, aluminum magnesium hydroxy myristate powder (15% moisture) from Example 4 were weighed into a closed 1 m³ mixer (Type: Becomix, Bremen) and homogeneously suspended over a period of 30 minutes with vigorous stirring. Subsequently, the suspension was heated to 120° C., which resulted in a steam pressure of approximately 1.6 bar. These conditions were maintained for 30 minutes. Subsequently, a vacuum was drawn and regulated so that the temperature did not drop significantly below 110° C. The gel formation process was complete when the water was completely evaporated; i.e., under vacuum a constant temperature of 120° C. was established.

Subsequently, the gel product was cooled to 100° C. and filled into barrels. In these containers, the finished gel was cooled to room temperature.

The yield of white, isopropyl palmitate lipogel obtained was 269 kg (90%).

EXAMPLE 7

Production of an isopropyl myristate lipogel.

3200 g of isopropylmyristate and a 2.286 g filter cake of the aluminum magnesium hydroxy stearate/palmitate (65% moisture) from Example 1 were weighed into a closed laboratory mixer (maximum capacity 5 kg) and, with vigorous stirring, homogeneously suspended over a period of 30 minutes. Subsequently, the suspension was heated to 120° C., resulting in a steam pressure of approximately 1.8 bar. These conditions were maintained for 30 minutes. Subsequently, a vacuum was slowly drawn and regulated so that the temperature did not drop significantly below 110° C. The gel formation process was complete when the water was completely evaporated; i.e., a constant temperature of 120° was reached under vacuum. Subsequently the gel product was slowly cooled to room temperature over a period of 2 hours.

The yield of white, isopropyl myristate lipogel obtained was 3975 g (99%).

EXAMPLE 8

Production of a paraffin oil lipogel.

1600 g of viscous white mineral oil and 430 g of the spray dried, aluminum magnesium hydroxy stearates (7% moisture) from Example 2 were weighed into a closed laboratory mixer (maximum capacity 5 kg) and homogeneously suspended over a period of 10 minutes with vigorous stirring. Subsequently, 40 g of completely demineralized water were added to the suspension, which was then stirred again for 20 min. and heated to 120° C. Owing to the water vapor, a pressure of approximately 1.6 bar resulted. These conditions were maintained for 30 minutes. Subsequently, a vacuum was slowly drawn and regulated so that the temperature did not drop significantly below 110° C. The gel process is complete when the water is completely evaporated; i.e., under vacuum a constant temperature of 120° C. was reached. Then, the gel product was slowly cooled to room temperature over a period of one hour.

The yield of colorless, slightly transparent, paraffin oil lipogel obtained was 1980 g (99%).

In the following Examples 9-11, the much improved thermostability of the new lipogels, as well as some characteristic features, for example, their suitability as suspension-aiding substances, are demonstrated.

EXAMPLE 9

The stability of the consistency of aluminum magnesium hydroxy fatty acid lipogels was examined as follows.

The consistency of the gels was determined according to the Klein microcone penetration method at different temperatures and the results are summarized in Table 1.

TABLE 1

| | Micropenetration (0.1 mm): | | |
|---|---|---|---|
| | 25° C. | 40° C. | 60° C. |
| Gel from Example 8 | 25 | 28 | 38 |
| Gel from Example 7 | 31 | 34 | 42 |

TABLE 1-continued

| | Micropenetration (0.1 mm): | | |
|---|---|---|---|
| | 25° C. | 40° C. | 60° C. |
| Gel from Example 6 | 35 | 38 | 42 |
| Gel from Example 5 | 40 | 41 | 46 |
| Paraffin oil bentonite gel | 74 | 96 | 109 |
| Isopropyl myristate bentonite gel | 60 | 65 | 84 |

As may be seen from Table 1 above, hardly any changes in consistency occurred at the temperatures tested. In contrast to the prior art's, organically-modified bentonite gels, inventive lipogels according to Examples 5 to 8 were significantly more solid at room temperature and were significantly more stable at elevated storage temperatures with respect to their viscosity. This is a very important characteristic for the production and storage of certain cosmetic products. For example, conventional sun protection formulations become liquid at the usual ambient temperatures reached outdoors in the summer time, and color pigments settle when lipsticks are cast at approximately 60° C. However, if rheological additives are present, such as, for example, gels from Examples 5 to 8, the viscosity and consistence of the products can be kept advantageously constant at higher temperatures.

EXAMPLE 10

The storage stability of aluminum magnesium hydroxy fatty acid lipogels at increased temperatures was tested as follows.

Storage stability was determined by visual evaluation of the degree of any oil separation at different temperatures in a climatic test cabinet, as well as by measurement of the consistency of the gels according to the Klein microcone penetration method. Evaluation key: x=stable, xx=beginning of oil separation, and xxx=obvious oil separation.

TABLE 2

| | Micropenetration (0.1 mm) | | | |
|---|---|---|---|---|
| | at beginning of storage | after 3 mos. storage at 50° C. | after 3 mos. at room temp. | after 3 mos. at 50° C. |
| Gel from Ex. 8 | 25 | 29 | x | x |
| Gel from Ex. 7 | 31 | 36 | x | x |
| Gel from Ex. 6 | 35 | 40 | x | x |
| Gel from Ex. 5 | 40 | 43 | x | xx |

The beginning of separation of the gels from Example 5 after three months at 50° C. can be explained by evaporation of the volatile silicone oil therefrom. Other than that, no oil separation was observed in any of the inventive gels tested. The lipogels from Examples 5 thru 8 show, in comparison to the prior art gels from, for example, the inventors' prior Federal Republic of Germany Published Patent Application No. 3,732,265, even further improvement with respect to stability. As already known from Table 14 of Federal Republic of Germany Published Patent Application No. 3,732,265, organically-modified bentonite gels show obvious oil separation after one week of storage at 50° C. The gels prepared according to Federal Republic of Germany Published Patent Application No. 3,732,265, by contrast, do not show any changes after one week, not even after one month. In a so-called heat stress test, which is customary in the cosmetics industry, however, these gels show a slight oil separation after approximately three months at 50° C. The gels of Examples 6 thru 8 of the present invention, however, are absolutely stable and the gel of Example 5 is very stable.

EXAMPLE 11

The settling behavior of an antiperspirant aerosol formulation was tested as follows.

In order to test the effectiveness of lipogels as antisettling substances in aerosols containing solid substances, the following antiperspirant formulations A thru D were produced as listed in Table 3.

TABLE 3

| | Aerosol Samples: | | | |
|---|---|---|---|---|
| | A | B | C | D |
| Gel from Example 5 | 7.25 | — | — | — |
| Gel from Example 7 | — | 7.25 | — | — |
| Silicon dioxide | — | — | 1.00 | — |
| Cyclomethicone pentamer | 4.50 | 4.50 | 4.50 | 4.50 |
| Isopropyl myristate | 5.00 | 5.00 | 11.25 | 12.25 |
| Aluminum chlorohydrate powder | 8.25 | 8.25 | 8.25 | 8.25 |
| n-Pentane | 40.00 | 40.00 | 40.00 | 40.00 |
| Propane/butane 2.7 bar | 35.00 | 35.00 | 35.00 | 35.00 |

PRODUCTION

The indicated amounts in grams of cyclomethicone pentamer and isopropyl myristate are provided and the gels and silicon dioxide are stirred into them until a homogeneous distribution results. Subsequently, aluminum chlorohydrate powder was added with stirring, homogenized using an Ultra Turrax Stirrer for 30 sec., and then deaerated under a vacuum. The corresponding quantity of n-Pentane was added to the paste made in this manner, the mixture was filled into glass aerosol bottles, which were then sealed and pressurized with the propane/butane mixture.

Sedimentation behavior may be observed and evaluated very well in situ in the glass aerosol bottles. For this purpose, the bottles were vigorously shaken four times in the vertical direction and then allowed to stand. Sedimentation was visually evaluated as a solid/liquid sedimentation interface. The distance from the bottom of each bottle to the top of the total filled-in amount of 100 ml is measured and set to equal 0% sedimentation. The interface or border region of the settling solid material is measured at different time intervals and proportioned to 0% sedimentation.

TABLE 4

| | % sedimention of solid ingredients after: | | | | | |
|---|---|---|---|---|---|---|
| | 0.5 min. | 1 min. | 5 min. | 10 min. | 20 min. | 60 min. |
| A | 0% | 7% | 21% | 35% | 50% | 57% |
| B | 0% | 0% | 7% | 14% | 28% | 40% |
| C | 33% | 30% | 58% | 64% | 65% | 65% |
| D | 100% | 100% | 100% | 100% | 100% | 100% |

EVALUATION

Aerosol D, without anti-sedimentation agent, settled immediately and formed a solid deposit on the bottom of the glass aerosol bottle. The aluminum chlorohydrate powder was very lumpy and clogged the aerosol valve. Spraying of the aerosol became impossible.

Aerosol C also settled very rapidly, while aerosols A and B kept the solid matter in suspension for a long time. A film of aerosols A and B sprayed onto the skin, however, resulted in a pronouncedly softer feeling of the skin in contrast to aerosol C. Aerosol C, moreover, tended to clog the valve after standing for a period of time, while aerosols A and B, which contain the gelling agent, i.e., anti-sedimentation agent, according to the invention can be emptied completely and evenly.

All of these tests show that the novel thermostable lipogels according to the invention demonstrate considerable technical advantages over conventional gels.

FIG. 1 shows the X-ray diffraction spectrum of the compound of Example 2. In general the three-dimensional structure of the aluminum magnesium hydroxy compounds according to the invention are characterized by a negatively changed intermediate layer, which may comprise anions of the most different types and water, as well as regularly-alternating octahedral layers which are composed of the cations of Al and Mg in a ratio of 2:1. The sequence of reflexes 003, 006, 009, 018, 110 and 113 is a sure indication of stacking of the octahedral layers.

The compounds according to the invention have been made hydrophobic by means of the organic lipophilic compounds.

Table 5 shows the corresponding evaluation of the spectrum of FIG. 1:

TABLE 5

X-ray spectrum of the compound according to Example 2 (Apparatus: Phillips Automated X-Ray Diffractometer System APD 15):

| Peak Nr. | 2-Theta | d(nm) | I/Io |
|---|---|---|---|
| 1 | 3.467 | 25.4602 | 98 |
| 2 | 5.155 | 17.1274 | 100 |
| 3 | 10.384 | 8.5121 | 25 |
| 4 | 10.624 | 8.3202 | 38 |
| 5 | 11.164 | 7.9184 | 75 |
| 6 | 19.962 | 4.4442 | 46 |
| 7 | 21.308 | 4.1662 | 17 |
| 8 | 21.909 | 4.0534 | 25 |
| 9 | 22.402 | 3.9653 | 33 |
| 10 | 22.599 | 3.9312 | 35 |

It will be understood that the above description of the present invention is susceptible to various modifications, changes and adaptations, and the same are intended to be comprehended within the meaning and range of equivalents of the appended claims.

What is claimed is:

1. An aluminum magnesium hydroxy fatty acid compound having the general formula:

$$Al_xMg_y(OH)_{3x+2y-z}R_z.nH_2O$$

Wherein R is at least one aliphatic monocarboxylic acid group having the formula $RCOO^-$ and comprising from 12 to 22 carbon atoms, and wherein $x=2$, $2 \leqq y \leqq 10$, $z=2$, and n is an integer greater than zero, the aluminum magnesium hydroxy fatty acid compound being prepared by the process comprising:

a. placing water and a slat selected from the group consisting of an alkali metal salt of at least one aliphatic monocarboxylic acid having from 12 to 22 carbon atoms and an ammonium salt of at least one aliphatic monocarboxylic acid having from 12 to 22 carbon atoms in a reactor fitted with heating means and stirring means;

b. dissolving the salt by intensive stirring using the stirring means and by heating using the heating means to a temperature ranging from 20° to 90° C. to provide a salt solution;

c. maintaining the pH of the salt solution in the reactor at a pH of at least 8 to provide an alkaline solution having a pH of at least 8 and a temperature ranging from 20° to 90° C.;

d. preparing an aqueous solution comprised of water and an aluminum salt which is soluble in water, and preparing an aqueous solution comprised of water and a magnesium salt which is highly soluble in water;

e. adding the aqueous solutions of step d to the reactor containing the alkaline solution of step c simultaneously and with constant stirring to cause reaction of the salt of step a, the aluminum salt of step d, and the magnesium salt of step d, and to cause precipitation of a precipitate comprised of an aluminum magnesium hydroxy fatty acid compound;

f. separating the precipitate from the solution of step e; and g. washing the precipitate with water which has been substantially demineralized until substantially no anions of the aluminum salt and the magnesium salt are detectable.

2. The aluminum magnesium hydroxy fatty acid compound according to claim 1, wherein the water employed in steps a through e of the process is water which has been demineralized so as to substantially exclude foreign ions from the reaction of step e.

3. The aluminum magnesium hydroxy fatty acid compound according to claim 1, wherein the aluminum salt is selected from the group consisting of an aluminum halide, an aluminum nitrate, an aluminum sulfate, a basic aluminum halide, and an alkali metal aluminate.

4. The aluminum magnesium hydroxy fatty acid compound according to claim 1, wherein the magnesium salt is selected from the group consisting of a magnesium halide, a magnesium nitrate, and a magnesium sulfate.

5. The aluminum magnesium hydroxy fatty acid compound according to claim 1, wherein the pH value of the solution during the reaction of step e is maintained by addition thereto of at least one hydroxide selected from the group consisting of an alkali metal hydroxide and ammonium hydroxide.

6. The aluminum magnesium hydroxy fatty acid compound according to claim 1, wherein the reactor is a closed reactor and wherein the closed reactor contains no carbon dioxide at least during the reaction of step e.

7. The aluminum magnesium hydroxy fatty acid compound according to claim 1, wherein the temperature employed during steps b and c ranges from 60° to 85° C.

8. The aluminum magnesium hydroxy fatty acid compound according to claim 1, wherein the reactor is a closed reactor and contains an inert gas at least during steps a thru e.

9. A thermostable lipogel, comprising:

an aluminum magnesium hydroxy fatty acid compound according to claim 1 (constituent a); and at least one organic lipophilic compound which is liquid at room temperature (20° C.) (constituent b), prepared by a process comprising:

reacting constituents a and b at a temperature ranging from 90° to 130° C. and a pressure of at least 1 bar while intensively stirring same.

10. The thermostable lipogel according to claim 9, wherein the at least one organic lipophilic compound is selected from the group consisting of a vegetable fat, a vegetable oil, an animal fat, an animal oil, a paraffin hydrocarbon, a silicon oil, an aliphatic ester, an aromatic ester, a higher alcohol and an ether.

11. The thermostable lipogel according to claim 9, wherein the thermostable lipogel has a concentration of the at least one organic lipophilic compound ranging from 70 to 90 weight percent.

12. The thermostable lipogel according to claim 11, wherein the concentration of the at least one organic lipophilic compound is 80 weight percent.

13. The thermostable lipogel according to claim 9, wherein the thermostable lipogel has a concentration of the aluminum magnesium hydroxy fatty acid compound ranging from 10 to 30 weight percent.

14. The thermostable lipogel according to claim 13, wherein the concentration of the aluminum magnesium hydroxy fatty acid compound is 20 weight percent.

15. The thermostable lipogel according to claim 11, wherein the thermostable lipogel has a concentration of the aluminum magnesium hydroxy fatty acid compound ranging from 10 to 30 weight percent.

16. The thermostable lipogel according to claim 15, wherein the concentration of the aluminum magnesium hydroxy fatty acid compound is 20 weight percent.

17. The process of preparing a preparation selected from the group consisting of a cosmetic preparation and a pharmaceutical preparation, comprising:
  including the thermostable lipogel according to claim 9 in the preparation as a rheological additive.

* * * * *

UNITED STATES PATENT AND TRADEMARK OFFICE
CERTIFICATE OF CORRECTION

PATENT NO. : 5,169,967

DATED : December 8th, 1992

INVENTOR(S) : Klaus SCHANZ, Uwe ASSMUS and Bruno KAUFMANN

It is certified that error appears in the above-identified patent and that said Letters Patent is hereby corrected as shown below:

On the Title Page,

Item: [75], change the sequence of the inventors to:

--Klaus SCHANZ, Dannstandt-Schauernheim;
Uwe ASSMUS, Reinheim; Bruno KAUFMANN,
Frankenthal, all of Fed. Rep. of Germany--.

Item: [75], change the spelling of "KAUMANN" to --KAUFMANN".

Signed and Sealed this

Twelfth Day of October, 1993

Attest:

BRUCE LEHMAN

Attesting Officer

Commissioner of Patents and Trademarks